United States Patent [19]

Brox et al.

[11] Patent Number: 5,103,060
[45] Date of Patent: Apr. 7, 1992

[54] COMPOUNDS WHICH ARE ETHYLENICALLY UNSATURATED IN THE TERMINAL POSITION, AND THE USE THEREOF IN NONLINEAR OPTICS

[75] Inventors: Wolfgang Brox; Dirk Funhoff, both of Heidelberg; Ulrike Licht, Mannheim; Harald Fuchs, Carlsberg; Wolfgang Schrepp, Heidelberg, all of Fed. Rep. of Germany

[73] Assignee: BASF Aktiengesellschaft, Ludwigshafen, Fed. Rep. of Germany

[21] Appl. No.: 571,286

[22] Filed: Aug. 23, 1990

[30] Foreign Application Priority Data

Sep. 1, 1989 [DE] Fed. Rep. of Germany ....... 3929053

[51] Int. Cl.⁵ .......................................... C07C 211/44
[52] U.S. Cl. .................... 564/441; 564/430; 564/305; 564/251; 558/418; 546/329
[58] Field of Search ................. 564/441, 305; 526/310; 528/10

[56] References Cited

U.S. PATENT DOCUMENTS

| | | | |
|---|---|---|---|
| 3,403,180 | 9/1968 | Soper | 564/441 |
| 4,358,391 | 11/1982 | Finkelmann et al. | 252/299.01 |
| 4,388,453 | 6/1983 | Finkelmann et al. | 528/15 |
| 4,762,912 | 8/1988 | Leslie et al. | 528/503 |

FOREIGN PATENT DOCUMENTS

| | | | |
|---|---|---|---|
| 0141512 | 5/1985 | European Pat. Off. | |
| 63210918A | 2/1987 | Japan | 564/441 |
| 2204053A | 11/1988 | United Kingdom | |
| 2209169 | 5/1989 | United Kingdom | |

OTHER PUBLICATIONS

Rothamsted et al., Index Chemicu, 27, 87559, 1967.

Carr et al., Makromolecular Chemistry, Rapid Communication, 8, 487–493 (1987).

*Primary Examiner*—Richard L. Raymond
*Assistant Examiner*—Shailendra Kumar
*Attorney, Agent, or Firm*—Keil & Weinkauf

[57] ABSTRACT

The novel compounds of the general formula I $$CH_2=CH-X-\underset{\underset{R}{|}}{N}-Y \qquad (I)$$

where
X is straight-chain or branched alkanediyl having from 1 to 20 carbon atoms or
X is straight-chain or branched alkanediyl having from 2 to 20 carbon atoms, whose carbon chain is interrupted by —O—, —S— and/or —NR—,
R is hydrogen, straight-chain or branched alkyl having from 1 to 6 carbon atoms or cycloalkyl, and
Y is a non-centrosymmetric radical containing an easily polarized conjugated π-electron system and at least one terminal electron-acceptor group, having nonlinear optical properties, are highly suitable as nonlinear optical materials for nonlinear optical arrangements and for the preparation of polymers having nonlinear optical properties. In particular, they can be used to prepare organopolysiloxanes having nonlinear optical properties and containing side groups of the general formula Ia $$-CH_2-CH_2-X-\underset{\underset{R}{|}}{N}-Y \qquad (Ia)$$

in which the variables are as defined above. These novel organopolysiloxanes having nonlinear optical properties are also highly suitable for the production of Langmuir-Blodgett layers.

2 Claims, No Drawings

COMPOUNDS WHICH ARE ETHYLENICALLY UNSATURATED IN THE TERMINAL POSITION, AND THE USE THEREOF IN NONLINEAR OPTICS

The present invention relates to the novel compounds of the general formula I $$CH_2=CH-X-N\overset{R}{-}Y \qquad (I)$$

where

X is straight-chain or branched alkanediyl having from 1 to 20 carbon atoms or

X is straight-chain or branched alkanediyl having from 2 to 20 carbon atoms, whose carbon chain is interrupted by —O—, —S— and/or —NR—, R is hydrogen, straight-chain or branched alkyl having from 1 to 6 carbon atoms or cycloalkyl, and Y is a non-centrosymmetric radical containing an easily polarized conjugated $\pi$-electron system and at least one terminal electron-acceptor group, which have nonlinear optical properties.

The present invention also relates to the use of the novel compounds I in nonlinear optics and for the preparation of novel polymers having nonlinear optical properties.

Nonlinear optics are very generally concerned with the interaction between electromagnetic fields in various substances and the associated field-dependent refractive index in these substances.

Very generally, a substance emits light if it contains dipoles vibrating at the frequency of the emitted light wave. If the vibrating dipoles contain a plurality of frequency components, these are all present in the light emitted by the particular substance. If the spatial elongation of the substance is greater than the wavelength of the emitted light, the identical dipoles vibrating in the substance should as far as possible vibrate in the same direction and with a phase difference which ensures that the light emitted by a volume element is not extinguished again by destructive interference with the light emitted by another volume element.

In a polarizable substance, a macroscopic polarization $\vec{P}$, defined as the dipole moment per volume, is caused by an externally applied electrical field $\vec{E}$.

If the polarizable substance does not contain any permanent molecular dipoles, the dipole moment, and thus the macroscopic polarization $\vec{P}$, results from the shift of the electrons by an amount $\vec{d}$ from their rest position, ie. the center of the positive charge. By contrast, if the polarizable substance contains permanent dipoles, the permanent dipole moment changes by the same mechanism due to the applied electrical field $\vec{E}$.

So long as the shift $\vec{d}$ remains proportional to the electrical field $\vec{E}$, the polarization $\vec{P}$ is also proportional to the electrical field $\vec{E}$, which is shown in the known linear equation 1

$$\vec{P}=\epsilon_0\chi\vec{E} \qquad Eq. 1,$$

in which $\epsilon_o$ is the absolute dielectric constant and $\chi$ is the dielectric susceptibility.

If the externally applied electrical field $\vec{E}$ is increased, each substance must naturally exhibit a deviation from the linear law as shown in equation 1 above a field strength which is specific for that substance. The mechanical analogy to this is the deviation from Hooke's law when a spring is overloaded. Such deviations from linearity can be treated mathematically most simply by adding a parabola and higher powers of the variables, ie. the nonlinear function is developed by powers of the variables $\vec{E}$, giving equation 2

Eq. 2, the basic equation of nonlinear optics. In this equation
$\chi^{(1)}$ is the first order dielectric susceptibility, which is in the end responsible for the linear optical behavior of the particular substance, $\chi^{(2)}$ is the second order dielectric susceptibility, which causes the second order nonlinear optical behavior of the particular substance, and $\chi^{(3)}$ is the third order dielectric susceptibility, on which the third order nonlinear optical behavior of the particular substance is based.

Both $\chi^{(2)}$ and $\chi^{(3)}$ are material constants which are dependent on the molecular structure, the crystal structure, light frequency and generally also the temperature. As is known, they can be determined using the "four-wave mixture" dynamic holographic method, as described by W. W. Schkunow et al. in Spektrum der Wissenschaft, February 1986, pages 92 to 97, and J. P. Huignard et al. in SPIE Volume 215, Recent Advances in Holography, 1980, pages 178 to 182.

Substances having a field-dependent dielectric susceptibility $\chi^{(2)}$, i.e. having second order nonlinear optical properties, result in a number of dispersive processes, such as frequency doubling (second harmonic generation, SHG), which allows the production of light of half the wavelength of the incident light, the electrooptical effect (Pockels effect), which facilitates a change in the refractive index in an applied electrical field, or sum and difference frequency mixing and frequency mixing, which permits continuous adjustment of laser light, resulting in a large number of industrial applications, for example electrooptical switches, frequency and intensity control in laser technology, holography, information processing and integrated optics.

Substances having a field-dependent dielectric susceptibility $\chi^{(3)}$, i.e. having third order nonlinear optical properties, are suitable, inter alia, for the production of purely optical switches and thus as waveguides for the design of purely optical computers.

Further possible applications are described in the publication by

D. R. Ulrich, "Nonlinear Optical Polymer Systems and Devices", in Molecular Crystals and Liquid Crystals, Volume 180, 1988, pages 1 to 31.

This article also describes the increasing importance of polymers having nonlinear optical properties, which it is hoped will be distinguished by addressing times of less than one picosecond, high, nonresonant nonlinearity, low dielectric constants in direct currents, low switching energy, a broad frequency range, low absorption, the absence of diffusion problems, the possibility for resonance amplification, simple manufacture and processibility and the possibility of easy modification,
possibility of handling and using at room temperature,
stability to environmental effects and
mechanical and structural stability,
and will therefore increasingly replace the long-known inorganic and organic crystalline substances having nonlinear optical properties.

As is known, the polymers described in the article by D. R. Ulrich, like all substances, have third order linear optical and nonlinear optical properties, but, by contrast, second order nonlinear optical properties depend on the presence of a non-centrosymmetric molecular structure and/or a non-centrosymmetric molecular arrangement in the crystal. In addition, a polymer must have a dielectric susceptibility $\chi^{(2)}$ of at least $10^{-8}$ esu, preferably $10^{-7}$ esu, to be suitable for the above-mentioned applications, which makes high demands on the molecular structure of the polymer as such, its ability to be prepared and the ability of the groups present therein having second order nonlinear optical properties to be spatially aligned uniformly. Only when these requirements are satisfied can the other advantages which are inherent in the polymers, or which are hoped for, be utilized or realized.

Ordered monomolecular layers are also known. They are formed by compounds which contain a polar and therefore hydrophilic molecular end and a nonpolar and therefore hydrophobic long-chain radical. Compounds of this type are generally also known as amphiphiles. To form the layers, the amphiphiles are placed on a water surface, on which they spread, their polar ends immersing in the aqueous phase and their hydrophobic long-chain radicals projecting out of the aqueous phase. If the compounds are then compressed on the water surface by means of a barrier, they become ordered from a certain surface force to form an ordered monomolecular layer in which the hydrophobic long-chain radicals are spatially aligned in a uniform manner. The transition into an ordered monomolecular layer of this type can be seen from a large force jump in the force-area diagram recorded during the compression of the particular compound. This force jump results from the increased resistance of the monomolecular layer now it is ordered to further compression by the barrier.

The ordered monomolecular layer produced in this way can easily be transferred onto the surface of carriers. This is usually done by dipping the carrier into the aqueous phase and withdrawing it again, which causes the ordered monomolecular layer to be transferred from the water surface to the carrier surface, the nonpolar ends of the molecules adhering to the carrier surface in the case, for example, of hydrophobic surfaces, such as pure silicon. If this transfer is complete, one generally refers to a transfer ratio of 1.

At least one further layer of this type can be applied to the surface of the ordered monomolecular layer on the carrier. In this case, this further ordered monomolecular layer is usually applied to the first layer in such a manner that the polar ends of the molecules in the two layers face one another. This spatial arrangement is also known as the head-head-tail-tail orientation or as Y deposition. If a third layer is applied to this double layer, it arranges itself in a corresponding manner so that its hydrophobic long-chain radicals face the corresponding radicals of the second layer, but, by contrast, the polar ends of its molecules point outward.

If the compounds of which these ordered monomolecular multilayers consist have a permanent dipole moment, Y deposition results in a macroscopic polarization P, which goes back only to the uppermost of the layers, only in the case of an odd number of superimposed layers. An even number of layers naturally results in a macroscopic polarization P of zero, since the dipole moments of the individual layers cancel each other out due to their mutual alignment.

If, by contrast, it is desired at least approximately to achieve the maximum possible macroscopic polarization P of an ordered monomolecular multilayer applied in Y deposition, it is necessary to include in Y deposition ordered monomolecular layers of compounds having no dipole moment between the individual layers of compounds having a permanent dipole, which results in an alternating layer sequence in which all the permanent dipoles present are aligned in a uniform manner.

As is known, both the ordered monomolecular monolayers and the corresponding multilayers are known as Langmuir-Blodgett layers. The method and equipment used to produce these layers are usually summarized under the term Langmuir-Blodgett technique. For reasons of brevity, only these specialist terms will be used hereinafter.

Compounds having nonlinear properties are disclosed, for example, in GB-A-2,204,053. These are azo compounds which can be prepared in a conventional manner by the azo coupling of 4-tetradecylaniline and naphth-2-ol, naphth-1-ol or 1-naphthylamine, of 4-nitroaniline and 1-naphthylamine or 1-(N-tetradecyl)-naphthylamine, of 4-aminobenzoic acid and 1-(N-tetradecyl)naphthylamine, of 4-aminobenzonitrile and 1-(N-tetradecyl)naphthylamine or 1-(N-heptyl)naphthylamine, of 4-aminobenzoic acid and N-decyl-N-methyl-m-toluidine and of 4-aminobenzonitrile and N-tetradecylaniline. Although these known compounds can be used in nonlinear optics and for the production of Langmuir-Blodgett layers, they do not, however, contain any ethylenically unsaturated groups in a terminal position and are thus not suitable for the preparation of polymers having nonlinear optical properties.

Compounds such as 4-(9-decenethia)-4'-cyano stilbene and 4-(4-pentenoxy)-4'-nitrobiphenyl, which have nonlinear optical properties and are also suitable for the preparation of polymers, in particular organopolysiloxanes, having nonlinear optical properties, are disclosed in U.S. Pat. No. 4,762,912, which also discloses an organopolysiloxane containing 5-(4'-nitrobiphenyl-4-oxy)pent-1-yl radicals as side groups having nonlinear optical properties. Further organopolysiloxanes of this type containing 4-(4'-cyanobiphenyl-4-oxy)but-1-yl, 5-(4'-cyanobiphenyl-4-oxy)pent-1-yl or 6-(4'-cyanobiphenyl-4-oxy)hex-1-yl radicals are disclosed in EP-A-0,141,512. However, it is not indicated in this publication whether these side groups of the organopolysiloxanes have nonlinear optical properties.

In both U.S. Pat. No. 4,762,912 and EP-A-0,141,512, the uniform spatial alignment of the side groups of the organopolysiloxanes which is necessary to utilize the second order nonlinear optical properties is effected by melting and solidifying the polymers to form a type of glass, the side groups aligning spatially in a uniform manner due to their liquid-crystalline properties. Neither is it indicated whether the substituted organopolysiloxanes as described therein are suitable for the production of Langmuir-Blodgett layers.

It is an object of the present invention to provide novel compounds which are easily obtainable, have nonlinear optical properties and are suitable for the preparation of novel polymers having nonlinear optical properties, in particular of novel organopolysiloxanes containing side groups having nonlinear optical properties. The novel polymers, in particular the novel organopolysiloxanes, should also be suitable for producing Langmuire-Blodgett layers in which the side groups having nonlinear optical properties are spatially aligned in a uniform manner so that the novel polymers can be used as novel nonlinear optical materials in novel nonlinear optical arrangements.

We have found that, surprisingly, this object is achieved by the novel compounds of the general formula I having nonlinear optical properties defined at the outset. In view of the prior art, it was surprising that the novel compounds of the general formula I having nonlinear optical properties are particularly suitable for the preparation of novel polymers having nonlinear optical properties, in particular of novel organopolysiloxanes containing side groups having nonlinear optical properties. It was also surprising that these novel organopolysiloxanes form Langmuir-Blodgett layers very easily.

The present invention accordingly provides the novel compounds of the general formula I having nonlinear optical properties defined at the outset. For brevity, these compounds are hereinafter referred to as "compounds I according to the invention".

The compounds I according to the invention are described by means of the general formula I, in which the variable X is either straight-chain or branched alkanediyl having from 1 to 20 carbon atoms or straight-chain or branched alkanediyl having from 2 to 20 carbon atoms whose carbon chain is interrupted by —O—, —S— and/or —NR—.

Examples of suitable straight-chain or branched alkanediyl having from 1 to 20 carbon atoms are methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene, eicosamethylene, ethane-1,1-diyl, propylene, 2,3-butylene, 2,3-dimethylbutane-1,4-diyl, 1-methylhexane-1,6-diyl, 2,2,4,4-tetramethylhexane-1,6-diyl, 2,2-dimethylpropane-1,3-diyl, 2-oxapropane-1,3-diyl, 2-thiapropane-1,3-diyl, 3-oxapentane-1,5-diyl, 3,6-dioxaoctane-1,8-diyl, 3-thiapentane-1,5-diyl, 2-azapropane-1,3-diyl, 2-methyl-2-azapropane-1,3-diyl, 3-azapentane-1,5-diyl, 3-azapentane-1,4-diyl, 3-ethyl-3-azapentane-1,5-diyl, 3,6-diazaoctane-1,8-diyl, 3,6-dimethyl-3,6-diazaoctane-1,8-diyl and 3-methyl-3-aza-6-oxaoctane-1,8-diyl, of which methylene, ethylene, trimethylene, tetramethylene, pentamethylene, hexamethylene and 2-oxapropane-1,3-diyl are particularly suitable. Of these, methylene is very particularly preferred.

In the general formula I, R is either hydrogen, straight-chain or branched alkyl having from 1 to 6 carbon atoms or cycloalkyl.

Examples of suitable straight-chain or branched alkyl radicals having from 1 to 6 carbon atoms are methyl, ethyl, propyl, isopropyl, n-butyl, sec.-butyl, tert.-butyl, n-pentyl and n-hexyl.

Examples of suitable cycloalkyl radicals are cyclopentyl and cyclohexyl.

Of these, the methyl radical is particularly preferred according to the invention.

In the general formula I, Y is a non-centrosymmetric radical containing an easily polarized conjugated π-electron system and at least one terminal electron-acceptor group.

Examples of suitable non-centrosymmetric radicals Y containing an easily polarized conjugated π-electron system and at least one terminal electron-acceptor group are:

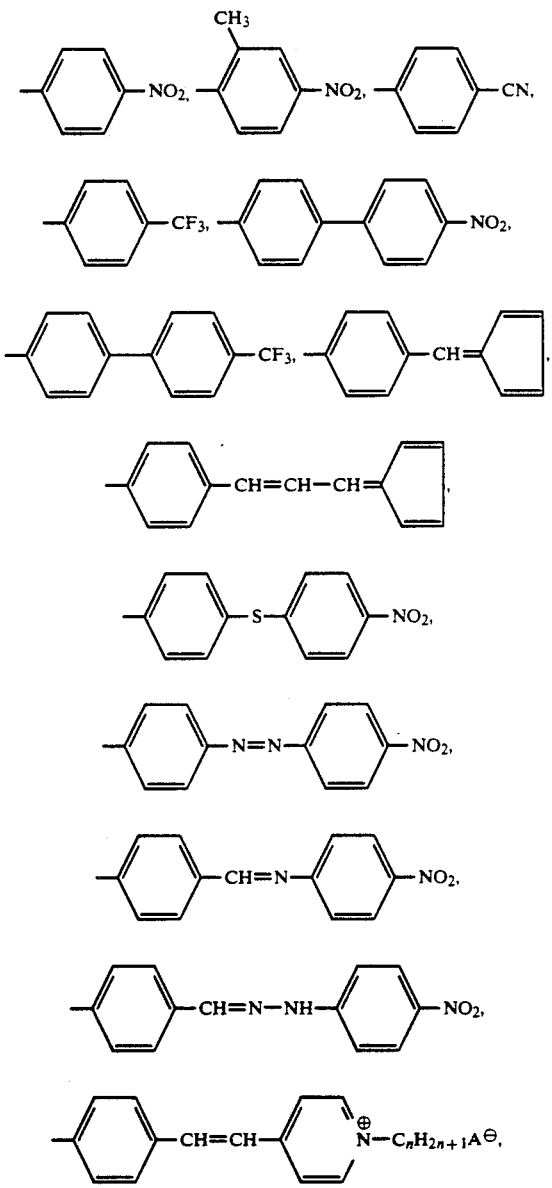

in which n is an integer from 1 to 22 and A⊖ is a conventional acid anion, such as Cl⊖, Br⊖ or HSO₄⊖;

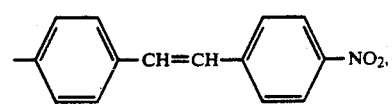

-continued

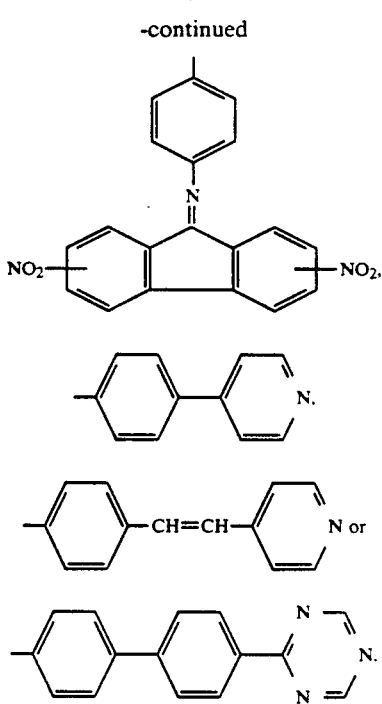

Examples of highly suitable radicals Y are those which contain a nitro, cyano, trifluoromethyl or fulven-6-yl group as the terminal electron-acceptor group, since the compounds I according to the invention containing one of these highly suitable radicals Y have particularly good applicational properties.

Examples of advantageous compounds I according to the invention are accordingly the compounds I-1 to I-8, according to the invention,

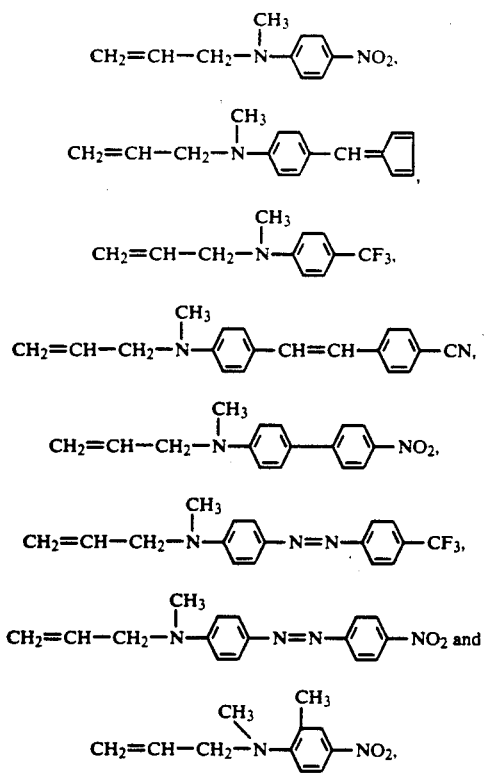

of which the compounds I-7 and I-8 according to the invention are particularly advantageous.

The method for the preparation of the compounds I according to the invention has no special features; indeed, synthetic methods which are conventional in low-molecular-weight organic chemistry are used. Thus, for example, the particularly advantageous compound I-7 according to the invention can be prepared by alkylating N-methylaniline using allyl chloride in toluene in the presence of triethylamine and reacting the resultant N-methyl-N-allylaniline with the diazonium salt, prepared in a conventional manner, of 4-nitroaniline.

The particularly advantageous compound I-8 according to the invention can be prepared, for example, by formylating 2-methyl-4-nitroaniline using 95% strength formic acid, alkylating the resultant N-formyl-2-methyl-4-nitroaniline using allyl chloride under phase-transfer conditions and reducing the resultant N-allyl-N-formyl-2-methyl-4-nitroaniline. On the other hand, it is also possible to hydrolyze the intermediate N-allyl-N-formyl-2-methyl-4-nitroaniline to form N-allyl-2-methyl-4-nitroaniline, and to alkylate the latter using methyliodide to give the compound I-8 according to the invention. To this end, the intermediate N-allyl-2-methyl-4-nitroaniline can also be prepared by alkylating N-formyl-2-methyl-4-nitroaniline using allyl chloride. In addition, it is also possible to reduce the intermediate N-formyl-2-methyl-4-nitroaniline using a boron hydride in tetrahydrofuran to give the corresponding N-methyl derivative, which is subsequently alkylated using allyl chloride to give the compound I-8 according to the invention.

The compounds I according to the invention have numerous particular advantages.

Thus, they can easily be prepared from conventional precursors, some of which are commercially available. They have nonlinear optical properties, which make them highly suitable for use as nonlinear optical materials in nonlinear optical arrangements serving the purposes mentioned at the outset. The resultant novel nonlinear optical materials consist of at least one of the compounds I according to the invention or comprise at least one such compound I. Like the arrangements known hitherto, the novel nonlinear optical arrangements contain at least one carrier, which is matched to the particular application. In addition, the novel nonlinear optical arrangements contain at least one layer consisting at least one of the compounds I according to the invention or comprising at least one such compound I. Both the novel nonlinear optical materials and the novel nonlinear optical arrangements are superior to the conventional materials and arrangements due to the use of the compounds I according to the invention.

A further particular advantage of the compounds I according to the invention is that they are particularly suitable for the preparation of polymers having nonlinear optical properties. The compounds I according to the invention can themselves form polymers by free-radical addition polymerization or they can be introduced as side groups Ia having nonlinear optical properties $$-CH_2-CH_2-X-N-Y, \quad \overset{R}{\underset{}{}} \quad (Ia)$$

where X, R and Y are as defined above in detail, into the existing polymers by suitable reactions. Any suitable polymers can be used for this purpose.

However, it is advantageous according to the invention to use organopolysiloxanes containing hydrogen atoms bonded to silicon atoms, since the SiH groups concerned very easily undergo addition reactions with compounds which are ethylenically unsaturated in the terminal position, to form SiC single bonds. Reactions of this type and the organopolysiloxanes suitable for this purpose are known, for example, from the patents U.S. Pat. No. 4,762,912, U.S. Pat. No. 4,358,391, U.S. Pat. No. 4,388,453 and U.S. Pat. No. 4,410,570.

The resultant organopolysiloxanes according to the invention either consist of or comprise groups of the general formula II

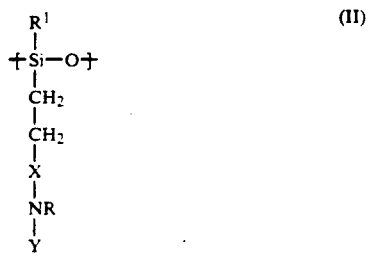

where X, R and Y are as defined above in detail. By contrast, $R^1$ is an aromatic radical, such as phenyl, or has the same meaning as R.

The particular advantages of the compounds I according to the invention also manifest themselves in the above-described organopolysiloxanes according to the invention. These also have excellent nonlinear optical properties, and can thus also be used as nonlinear optical materials in nonlinear optical arrangements of the type mentioned above.

In particular, the organopolysiloxanes according to the invention are suitable for the production of Langmuir-Blodgett monolayers and multilayers which either consist of only the organopolysiloxanes according to the invention or, in the case of multilayers, contain, in an alternating sequence, other Langmuir-Blodgett layers applied in Y deposition.

Particularly preferred Langmuir-Blodgett multilayers are those which contain Langmuir-Blodgett monolayers comprising at least one of the organopolysiloxanes according to the invention and Langmuir-Blodgett monolayers comprising at least one polymeric amphiphile in Y deposition and in an alternating sequence.

An example of a particularly suitable polymeric amphiphile is

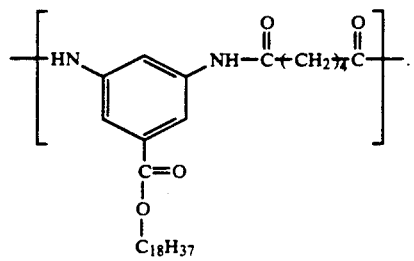

The method for the production of these Langmuir-Blodgett monolayers and multilayers according to the invention has no special features; indeed, they are produced by the conventional Langmuir-Blodgett technique described at the outset.

The side groups in the organopolysiloxanes according to the invention prove to be particularly easy to align spatially in a uniform manner without the need to employ side groups having liquid-crystalline properties, which are difficult to prepare, or processes to force them to align spatially in a uniform manner. In view of the use of the organopolysiloxanes according to the invention and the Langmuir-Blodgett layers according to the invention as nonlinear optical materials, this is a very great advantage.

If it is necessary at all during or after the spatial alignment of the side groups in the organopolysiloxanes according to the invention in a uniform manner by the Langmuir-Blodgett technique, the Langmuir-Blodgett monolayers and multilayers according to the invention can be produced using electrical and/or magnetic fields of suitable direction and sign and/or be subjected after their production, if desired in these fields, to conventional processes for domain growth, for example recrystallization or zone melting.

Accordingly, the organopolysiloxanes according to the invention are highly suitable for the production of novel nonlinear optical arrangements, as used, for example, for frequency doubling, frequency mixing or in optical waveguides or as are present in optical modulators, optical multiplexers, optical logical components or optical amplifiers.

These novel nonlinear optical arrangements contain at least one carrier matched to the particular application in form and function, for example a semiconductor chip, and at least one layer, in particular a Langmuir-Blodgett layer, which consists of or comprises at least one organopolysiloxane according to the invention.

When used in nonlinear optical arrangements, further particular advantages of the organopolysiloxanes according to the invention and of the Langmuir-Blodgett layers according to the invention become obvious; thus, their exact two-dimensional alignment results in a uniform thickness and the highest possible anisotropy of the layers concerned, which are also stable to intensive laser irradiation.

EXAMPLES

Example 1

Preparation and physical properties of the compound I-8 (N-allyl-N-methyl-2-methyl-4-nitroaniline) according to the invention:

Experimental procedure:

To prepare the compound I-8 according to the invention, first various starting materials are prepared, and then reacted in various ways to give the compound I-8 according to the invention.

1.1 Preparation of N-formyl-2-methyl-4-nitroaniline from 2-methyl-4-nitroaniline and formic acid 1000 g of formic acid were introduced into a flask fitted with a stirrer and a reflux condenser. 151 g (1 mol) of 2-methyl-4-nitroaniline were added, and the resultant mixture was slowly heated to the reflux point. After four hours, the reaction mixture was poured into 5 l of ice water. The resultant precipitate was filtered off with suction, washed with water until neutral and then dried at 60° C. under reduced pressure. Recrystallization of the resultant crude product from 2.5 l of methanol or ethanol gave 171 g of N-formyl-2-methyl-4-nitroaniline (yield: 95%) as yellow crystals, which melted at 162° C.

The purified compound also had the following physical/chemical properties:

R$_f$(aluminum oxide, ethyl acetate) = 0.6
$^1$H-NMR spectrum (270 MHz, d$_6$-dimethyl sulfoxide DMSO)
δ (ppm) = 9.85 (broad singlet s$_{br}$, 1H, NCHO)
8.50 (s$_{br}$, 1H, Ar—H)
8.25 (s$_{br}$, 1H, N—H)
8.05–8.00 (multiplet m, 2H, Ar—H)
2.38 (singlet s, 3H, CH$_3$)
$^{13}$C-NMR spectrum (67.9 MHz, D$_6$-DMSO)
δ (ppm) = 160.7, 143.1, 142.4, 129.1, 125.5, 122.2, 120.8, 17.8
IR-spectrum (KBr)
3380, 1710, 1585, 1529, 1505, 1460, 1339, 1325, 1274, 1260, 1144, 1120, 910, 855, 810, 755, 680 cm$^{-1}$ Elemental analysis (C$_8$H$_8$N$_2$O$_3$: 180.2)

| | | | |
|---|---|---|---|
| Calc.: | C 53.3 | H 4.5 | N 15.6 |
| Found: | C 52.9 | H 4.5 | N 15.5 |

1.2 Preparation of N-formyl-2-methyl-4-nitroaniline from 2-methyl-4-nitroaniline and formic acid/acetic anhydride 25 g (0.26 mol) of acetic anhydride were cooled to 0° C. under nitrogen. 15 g (0.32 mol) of formic acid were added dropwise at this temperature. The resultant mixture was then allowed to melt, and was then warmed to from 50 to 60° C. over the course of two hours. The mixture was then cooled to room temperature, and 20 ml of dry tetrahydrofuran were added, and the resultant mixture was again cooled to 0° C. A suspension of 15.2 g (0.1 mol) of 2-methyl-4-nitroaniline in 100 ml of THF was then added dropwise to this mixture, and the resultant mixture was left at 0° C. for one hour and then warmed to room temperature. The resultant yellow precipitate was filtered off with suction, washed with water and dried at 50° C. under reduced pressure, to give 13.9 g of N-formyl-2-methyl-4-nitroaniline (yield: 77%). The product had the same physical/chemical properties as that prepared in the above-described manner (compare section 1.1).

1.3 Preparation of N-allyl-N-formyl-2-methyl-4-nitroaniline from N-formyl-2-methyl-4-nitroaniline 155 g of potassium carbonate were introduced into 500 ml of dimethylformamide. 50 g (0.28 mol) of N-formyl-2-methyl-4-nitroaniline were added to this mixture to give an orange solution, which became blood-red after 128.6 g (136.8 ml, 1.68 mol) of allyl chloride were added. The resultant reaction mixture was stirred overnight and subsequently poured into 1.5 l of ice water. The crude product which deposited was extracted twice from the aqueous phase with 400 ml of dichloromethane in each case. The two combined dichloromethane phases were washed three times with 500 ml of water in each case, subsequently dried over sodium sulfate and then evaporated, to give 58.3 g of N-allyl-N-formyl-2-methyl-4-nitroaniline (yield: 95%) as an orange oil which crystallized in the refrigerator. The product had a melting point of 56° C. and the following physical/chemical properties:

R$_f$(aluminum oxide, n-hexane/ethyl acetate, 3/1) = 0.3

$^1$H-NMR spectrum (270 MHz, D$_6$-DMSO)
δ (ppm) = 8.45 (s, 1H, NCHO)
8.25–8.05 (m, 2H, Ar—H)
7.55–7.50 (two doublets 2d, 1H, Ar—H)
6.00–5.75 (m, 1H, NCH$_2$CHCH$_2$)
5.25–5.10 (m, 2H, NCH$_2$CHCH$_2$)
4.40–4.35 (m, 2H, NCH$_2$CHCH$_2$)
2.4, 2.3 (two singlets, 2s, 3H, Ar—CH$_3$)
$^{13}$C-NMR spectrum (67.9 MHz, D$_6$-DMSO)
δ (ppm) = 162.2, 162.1, 146.7, 145.4, 144.7, 138.5, 137.7, 133.8, 132.6, 129.7, 129.2, 126.2, 125.5, 122.1, 121.8, 119.7, 118.8, 52.3, 47.7, 18.1
IR-spectrum (KBr)
1673, 1518, 1487, 1420, 1390, 1343, 1207, 954, 807, 738 cm$^{-1}$ Elemental analysis (C$_{11}$H$_{12}$N$_2$O$_3$: 220.2)

| | | | |
|---|---|---|---|
| Calc.: | C 60.0 | H 5.5 | N 12.7 |
| Found: | C 59.9 | H 5.7 | N 12.2 |

1.4 Preparation of N-allyl-2-methyl-4-nitroaniline from N-allyl-N-formyl-2-methyl-4-nitroaniline 72 g (0.33 mol) of N-allyl-N-formyl-2-methyl-4-nitroaniline were dissolved in 500 ml of dimethylformamide. The resultant solution was heated to 70° C., and 300 g of 1 N sodium hydroxide solution were added. The resulting reaction mixture was left at 70° C. for 4 hours and subsequently poured into 3 l of ice water. The precipitate was filtered off with suction, washed with water and then dried at 50° C. under reduced pressure, to give 49.3 g of crude product (yield: 85.5%). The yellow material was dissolved in ethanol at 50° C., the solution was cooled to 5° C., and N-allyl-2-methyl-4-nitroaniline crystallized out in the form of yellow needles which melted at 58.5 to 59.5° C.

The purified product had the following physical/chemical properties:

R$_f$(aluminum oxide, n-hexane/ethyl acetate, 3/1) = 0.5

$^1$H-NMR spectrum (270 MHz, D$_6$-DMSO)
δ (ppm) = 7.95–7.90 (m, 2H, Ar—H)
6.55 (d, 1H, Ar—H)
6.50 (s, 1H, N—H)
6.00–5.85 (m, 1H, NCH$_2$CHCH$_2$)
5.25–5.15 (m, 2H, NCH$_2$CHCH$_2$)
4.00–3.90 (m, 2H, NCH$_2$CHCH$_2$)
2.25 (s, 3H, Ar—CH$_3$)
$^{13}$C-NMR spectrum (67.9 MHz, D$_6$-DMSO)
δ (ppm) = 152.5, 136.2, 134.9, 125.6, 124.2, 121.8, 115.8, 108.2, 45.2, 17.5
IR-spectrum (KBr)
3400, 1604, 1588, 1526, 1488, 1463, 1312, 1277, 1240, 1187, 1105, 960, 750 cm$^{-1}$ Elemental analysis (C$_{10}$H$_{12}$N$_2$O$_2$: 192.2)

| | | | |
|---|---|---|---|
| Calc.: | C 62.5 | H 6.3 | N 14.6 |
| Found: | C 62.4 | H 6.4 | N 14.7 |

The product was highly suitable for the preparation of the compound I-8 according to the invention.

1.5 Preparation of N-allyl-2-methyl-4-nitroaniline from N-formyl-2-methyl-4-nitroaniline in a one-pot process 60 g (0.33 mol) of N-formyl-2-methyl-4-nitroaniline were dissolved in 500 ml of dimethylformamide. 184 g (1.33 mol) of potassium carbonate were added, and the resultant solution was warmed to 50° C. 152.8 g (2 mol) of allyl chloride were added dropwise in the course of 50 minutes to the mixture at 50° C. When the alkylation reaction was complete, the resultant reaction mixture was warmed to 70° C. and 350 g of 1 N sodium hydroxide solution were slowly added dropwise. The resultant mixture was stirred at 70° C. for 2.5 hours and subsequently poured into 3 l of ice water. The precipitate was filtered off with suction, washed with water until neutral and subsequently dried at 50° C. under reduced pressure, to give 61 g of N-allyl-2-methyl-4-nitroaniline (yield: 95%), which was recrystallized as described under section 1.4 and then had the same physical chemical properties as the compound prepared in accordance with section 1.4.

The product obtained in this way was also highly suitable for the preparation of the compound I-8 according to the invention.

1.6 Preparation of the compounds I-8 according to the invention from N-allyl-2-methyl-4-nitroaniline 20 g (104 mmol) of N-allyl-2-methyl-4-nitroaniline were dissolved in 600 ml of dimethyl sulfoxide. 41.6 g (1.04 mol) of sodium hydroxide powder were added to the resultant solution, whereupon the solution became deep red. 44.3 g (19.6 ml, 312 mmol) of methyl iodide were added in one portion, and the solution became red-brown. The red-brown solution was stirred at room temperature for from 1 to 2 hours, poured into 3 l of ice water and then extracted three times with 500 ml of dichloromethane in each case. The combined dichloromethane phases were subsequently washed three times with 500 ml of water in each case, dried over sodium sulfate, filtered and evaporated under reduced pressure, to give a brown oil (21.4 g, corresponding to a yield of 99%), which was purified by chromatography on silica gel (eluent: n-hexane/ethyl acetate 15/1), to give N-allyl-N-methyl-2-methyl-4-nitroaniline (compound I-8 according to the invention) in a yield of 19.5 g, corresponding to 90%.

The compound I-8 according to the invention had the following physical/chemical properties:

B.p. ≃ 140–145° C./0.2 mmHg
$R_f$ (aluminum oxide, n-hexane/ethyl acetate, 15/1): 0.68
(silica gel, n-hexane/ethyl acetate, 15/1): 0.55
$^1$H-NMR spectrum (270 MHz, D$_6$-DMSO)
δ (ppm) =  8.00–7.85 (m, 2H, Ar—$\underline{H}$)
 7.05–7.00 (d, 1H, Ar—$\underline{H}$)
 5.95–5.80 (m, 1H, N—CH$_2$C$\underline{H}$CH$_2$)
 5.35–5.15 (m, 2H, N—CH$_2$CHC$\underline{H}_2$)
 3.70–3.65 (d, 2H, N—C$\underline{H}_2$CHCH$_2$)
 2.80 (s, 3H, N—C$\underline{H}_3$)
 2.35 (s, 3H, Ar—C$\underline{H}_3$)
$^{13}$C-NMR spectrum (67.9 MHz, D$_6$-DMSO)
δ (ppm) = 157.8, 140.7, 134.5, 130.3, 126.7, 122.4, 118.2, 117.5, 57.5, 39.7, 19.5
IR-spectrum (film)
1603, 1583, 1503, 1449, 1333, 1274, 1233, 1185, 1093, 933 cm$^{-1}$

| Elemental analysis (C$_{11}$H$_{14}$N$_2$O$_2$: 206.2) | | | |
|---|---|---|---|
| Calc.: | C 64.1 | H 6.8 | N 13.6 |
| Found: | C 64.0 | H 7.0 | N 13.7 |

The compound I-8 according to the invention was highly suitable as a nonlinear optical material. In particular, it was very suitable for the preparation of the organopolysiloxanes according to the invention containing side groups having nonlinear optical properties. It was again very easily possible to apply the organopolysiloxanes according to the invention in the form of Langmuir-Blodgett multilayers to suitable carriers, resulting in nonlinear optical arrangements having very good applicational properties.

1.7 Preparation of N-methyl-2-methyl-4-nitroaniline from N-formyl-2-methyl-4-nitroaniline 18 g (0.1 mol) of N-formyl-2-methyl-4-nitroaniline were introduced into 500 ml of dry tetrahydrofuran. 200 ml of a 1 molar solution of borane/tetrahydrofuran complex in tetrahydrofuran were added dropwise at 0° C. over the course of 45 minutes. The resultant reaction mixture was warmed to room temperature, refluxed for 1 hour, re-cooled to 0° C. and hydrolyzed using 130 ml of water. After the tetrahydrofuran had been evaporated, the residue remaining was taken up in 300 ml of 6 N hydrochloric acid, and the solution was refluxed for 2.5 hours, cooled and poured into 1 l of ice water. The yellow precipitate obtained was filtered off with suction, washed with water, dried at 50° C. under reduced pressure and recrystallized from ethanol, to give 15.8 g of the product (yield: 95%).

The recrystallized N-methyl-2-methyl-4-nitroaniline had the following physical/chemical properties:

Melting point: 139° C.
$R_f$(aluminum oxide, ethyl acetate) = 0.75
$^1$H-NMR spectrum (270 MHz, D$_6$-DMSO)
δ (ppm) =  8.00 (dd, 1H, Ar—$\underline{H}$)
 7.90 (s, 1H, Ar—$\underline{H}$)
 6.50 (d, 1H, Ar—$\underline{H}$)
 5.90 (S$_{br}$, 1H, N$\underline{H}$)
 2.90 (d, 3H, NC$\underline{H}_3$)
 2.15 (s, 3H, Ar—C$\underline{H}_3$)
$^{13}$C-NMR spectrum (67.9 MHz, D$_6$-DMSO)
δ (ppm) = 153.5, 135.8, 125.2, 124.5, 121.5, 107.2, 29.8, 17.3
IR-spectrum (KBr)
3387, 1611, 1589, 1544, 1490, 1325, 1263, 1165, 1096, 750 cm$^{-1}$

| Elemental analysis (C$_8$H$_{10}$N$_2$O$_2$: 166.2) | | | |
|---|---|---|---|
| Calc.: | C 57.8 | H 6.1 | N 16.9 |
| Found: | C 57.8 | H 6.2 | N 16.7 |

The product was again highly suitable for the preparation of the compound I-8 according to the invention.

1.8 Preparation of the compound I-8 according to the invention from N-methyl-2-methyl-4-nitroaniline N-Methyl-2-methyl-4-nitroaniline was alkylated under the conditions indicated in section 1.6, the only difference being that the methyl iodide was replaced by three times the molar amount of allyl chloride. The resultant compound I-8 according to the invention was isolated and purified as indicated under section 1.6, and also had the physical/chemical properties indicated therein and the same particular advantages and possible uses.

Example 2

Preparation and properties of the compound I-7 according to the invention

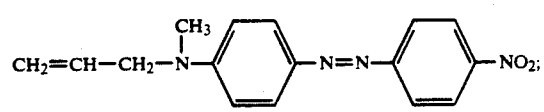

Experimental procedure

2.1 Preparation of N-allyl-N-methylaniline

For the preparation of the compound I-7 according to the invention, first N-allyl-N-methylaniline was prepared. To this end, 214 g (2 mol) of N-methylaniline and 202 g (2 mol) of triethylamine were dissolved in one liter of toluene, and the resultant solution was then warmed to from 80 to 85° C. 153 g (2 mol) of allyl chloride were added dropwise to the stirred solution, and the resultant reaction mixture was stirred at this temperature for 1.5 hours. When the reaction was complete, the precipitated triethylammonium chloride was filtered off and washed with 100 ml of toluene. The two toluene solutions were combined and evaporated under reduced pressure. The residue remaining contained 34% of unreacted N-methylaniline and 66% of N-allyl-N-methylaniline, which was obtained in a purity of 99.3% by distillation under reduced pressure (3 mbar, head temperature 75 to 76° C.). The product had the following $^1$H nuclear magnetic resonance spectrum:

$\delta$ (ppm) = 7.25–7.15 (m, 2H, Ar—$\underline{H}$)
6.75–6.70 (m, 3H, Ar—$\underline{H}$)
5.90–5.75 (m, 1H, N—CH$_2$C$\underline{H}$ = CH$_2$)
5.20–5.10 (m, 2H, N—CH$_2$—CH =·C$\underline{H}_2$)
3.90 (d, 2H, N—C$\underline{H}_2$—CH = CH$_2$)

2.2 Diazotization of 4-nitroaniline

For the preparation of the compound I-7 according to the invention, 4-nitroaniline was also diazotized. To this end, 27.6 g (0.2 mol) of 4-nitroaniline were brought to the boil in 100 ml of concentrated hydrochloric acid and 20 ml of water and then stirred into 200 ml of cold water. The resultant solution was cooled to $-10°$ C., and 48 ml of a 30% strength aqueous sodium nitrite solution was added dropwise at a rate such that the temperature was kept at $-10°$ C. The resultant reaction mixture was stirred for 30 minutes, and the excess sodium nitrite remaining was then destroyed using urea. The operation was monitored using potassium iodide paper and it was ensured that the temperature did not exceed 0° C.

2.3 Preparation of the compound I-7 according to the invention by azo coupling 29.4 g (0.2 mol) of N-allyl-N-methylaniline were dissolved in 30 ml of concentrated hydrochloric acid and 150 ml of water. This solution was added at $-10°$ C. to the diazonium salt of 4-nitroaniline. A pH of 4 was then established using about 100 g of potassium acetate causing the azo dye (the compound I-7 according to the invention) to be precipitated as a bulky red precipitate. The mixture was left to stand for 2.5 hours, and the red azo dye was filtered off with suction, washed with water until neutral and dried. The crude product obtained was recrystallized from ethanol to give dark green needles with a metallic luster. 42 g of the compound I-7 according to the invention were obtained, corresponding to a yield of 71%.

The product had the following physical/chemical properties:

Melting point: 120 to 120.5° C.
$R_f$(SiO$_2$, n-hexane/ethyl acetate, 3:1) = 0.58
$^1$H-NMR spectrum (250 MHz, CDCl$_3$)

$\delta$ (ppm) = 8.25/7.90 (coupling pattern of two rings of similar chemical shift of the AB system, 4H, Ar—$\underline{H}$)
7.90/6.65 (AB, 4$\underline{H}$, Ar—$\underline{H}$)
5.95–5.75 (m, 1H, N—C$\underline{H}_2$—C$\underline{H}$ = CH$_2$)
5.25–5.10 (m, 2H, N—CH$_2$—C$\underline{H}$ = C$\underline{H}_2$)
4.10 (d, 2H, N—C$\underline{H}_2$—CH = CH$_2$)
3.10 (s, 3H, N—C$\underline{H}_3$)

$^{13}$C-NMR spectrum (67.9 MHz, CDCl$_3$)
$\delta$ (ppm) = 157.0, 152.9, 147.7, 144.2, 132.2, 126.1, 126.1, 124.7, 124.7, 122.7, 122.7, 116.9, 111.8, 111.8, 54.9, 38.3

IR spectrum (KBr)
1601, 1586, 1519, 1508, 1379, 1333, 1308, 1135, 1105, 1097 cm$^{-1}$ The compound I-8 according to the invention had excellent nonlinear optical properties and was therefore highly suitable as a nonlinear optical material for the production of nonlinear optical arrangements. In particular, it was highly suitable for the preparation of organopolysiloxanes containing side groups having nonlinear optical properties, which could easily be formed into Langmuir-Blodgett multilayers which could be used, due to their excellent application properties, in novel nonlinear optical arrangements.

We claim:

1. A compound having non-linear optical properties of the formula I

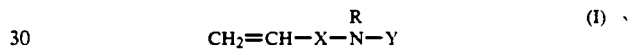

where

X is straight-chain or branched alkanediyl having from 1 to 20 carbon atoms or

X is straight-chain or branched alkanediyl having from 2 to 20 carbon atoms, whose carbon chain is interrupted by —O—, —S— and/or —NR—, R is hydrogen, straight-chain or branched alkyl having from 1 to 6 carbon atoms or C$_5$-C$_6$ cycloalkyl, and Y is a non-centrosymmetric radical containing an easily polarized conjugated $\pi$-electron system and at least one terminal electron acceptor group, selected from the group consisting of:

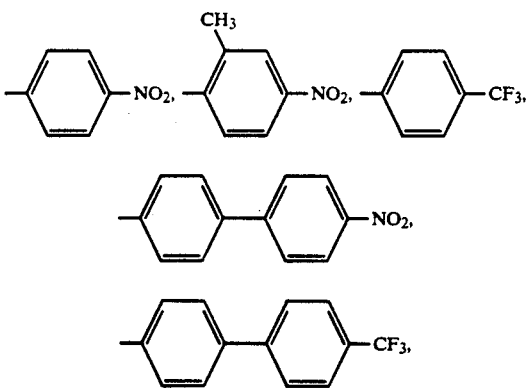

in which
n is an integer from 1 to 22 and A$^\ominus$ is a conventional acid anion.

2. The compound I as claimed in claim 1, wherein
X is methylene, ethylene, trimethylene, tetramethylene, pentamethylene, hexamethylene or 2-oxapropane-1,3-diyl, and
R is methyl.

* * * * *